United States Patent
Neumann

(10) Patent No.: US 11,651,413 B2
(45) Date of Patent: May 16, 2023

(54) METHODS AND SYSTEMS FOR CONNECTING FOOD INTERESTS WITH FOOD PROVIDERS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/890,796

(22) Filed: Jun. 2, 2020

(65) Prior Publication Data

US 2021/0374828 A1     Dec. 2, 2021

(51) Int. Cl.
*G06Q 30/06* (2012.01)
*G06Q 30/0601* (2023.01)
*G16H 20/60* (2018.01)
*G06Q 50/12* (2012.01)

(52) U.S. Cl.
CPC ......... *G06Q 30/0631* (2013.01); *G06Q 50/12* (2013.01); *G16H 20/60* (2018.01)

(58) Field of Classification Search
CPC .............. G06Q 30/0641; G06Q 50/12; G06Q 30/0631; G16H 20/60; G06N 20/00
USPC ...................................................... 705/26.7
See application file for complete search history.

(56) References Cited

U.S. PATENT DOCUMENTS

| | | | |
|---|---|---|---|
| 8,605,952 B2 | 12/2013 | Boushey et al. | |
| 8,920,175 B2 | 12/2014 | Black | |
| 2006/0199155 A1 | 9/2006 | Mosher | |
| 2014/0255882 A1* | 9/2014 | Hadad | G16H 20/60 434/127 |
| 2015/0228062 A1* | 8/2015 | Joshi | G06Q 50/12 382/110 |
| 2016/0012513 A1* | 1/2016 | Martinez | G06Q 30/0631 705/15 |
| 2016/0098942 A1 | 4/2016 | Messier | |
| 2016/0225284 A1 | 8/2016 | Schoen | |
| 2017/0193853 A1 | 6/2017 | Byron et al. | |
| 2019/0034836 A1* | 1/2019 | Chari | G06N 20/20 |
| 2019/0290172 A1* | 9/2019 | Hadad | A61B 5/0022 |
| 2019/0370916 A1* | 12/2019 | Surkin | G06Q 50/12 |
| 2020/0074879 A1 | 3/2020 | Murdoch et al. | |
| 2020/0312466 A1* | 10/2020 | Banerjee | G16H 30/20 |

* cited by examiner

*Primary Examiner* — Michelle T Kringen
(74) *Attorney, Agent, or Firm* — Caldwell Intellectual Property Law

(57) ABSTRACT

A system for connecting food interests with food providers, the system including a computing device configured to receive, from each of a plurality of remote devices located in a specified location, a plurality of inputs containing food interest data; calculate, using a first machine-learning process, a nourishment intake theme for each of the plurality of remote devices; detect, a plurality of food providers located within the specified location providing a nourishment provision; identify, using a second machine-learning process; compare a remote device containing the nourishment intake theme with a food provider that offers a nourishment provision that compares the nourishment intake theme; and support transmission of the nourishment provision that compares the nourishment intake theme to the remote device.

10 Claims, 5 Drawing Sheets

METHODS AND SYSTEMS FOR CONNECTING FOOD INTERESTS WITH FOOD PROVIDERS

FIELD OF THE INVENTION

The present invention generally relates to the field of artificial intelligence. In particular, the present invention is directed to methods and systems for connecting food interests with food providers.

BACKGROUND

Locating food providers that suggest food options that align with one's food interests can be difficult. Frequently, one can be tempted by foods that may not be ideal for one's body. Knowing which foods may align with one's food interests can be challenging given the multiplicity of channels and insurmountable options available.

SUMMARY OF THE DISCLOSURE

In an aspect, a system for connecting food interests with food providers, the system comprising a computing device, the computing device designed and configured to receive, from a first remote device of a plurality of remote devices located in a specified location, an input including food interest data; generating, as a function of a first machine-learning process, a nourishment intake theme for the remote device, wherein the first machine-learning process utilizes food interest data as an input, and outputs the nourishment intake theme; detect a plurality of food providers located within the specified location, wherein each of the plurality of food providers provides a nourishment provision; generating, as a function of a second machine-learning process, a nourishment provider theme for each of the plurality of food providers located within the specified location, wherein the second machine-learning process utilizes the nourishment provision as an input, and outputs the nourishment provider theme; compare, the first remote device having a first nourishment intake theme with a food provider theme; and support transmission of a nourishment provision that as a function of comparing the first nourishment intake theme to the nourishment provider theme.

In an aspect, a method of connecting food interests with food providers, the method comprising receiving by a computing device, from a first remote device of a plurality of remote devices located in a specified location, an input including food interest data; generating by the computing device, as a function of a first machine-learning process, a nourishment intake theme for the remote device, wherein the first machine-learning process utilizes food interest data as an input, and outputs the nourishment intake theme; detecting by the computing device, a plurality of food providers located within the specified location, wherein each of the plurality of food providers provides a nourishment provision; generating by the computing device, as a function of a second machine-learning process, a nourishment provider theme for each of the plurality of food providers located within the specified location, wherein the second machine-learning process utilizes the nourishment provision as an input, and outputs the nourishment provider theme; comparing by the computing device, the first remote device having a first nourishment intake theme with a nourishment provider theme; and supporting by the computing device, transmission of a nourishment provision as a function of comparing the first nourishment intake theme to the nourishment provider theme.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for connecting food interests with food providers. In an embodiment, a computing device receives a plurality of inputs containing food interests data. A first machine-learning process is utilized to calculate a nourishment intake theme for each of the plurality of inputs. A computing device generates as a function of a second machine-learning process a nourishment provider theme 144 for each of a plurality of food providers. A computing device compares a nourishment intake theme with a food provider that offers nourishment provisions that compare the nourishment intake theme.

Figure 1:
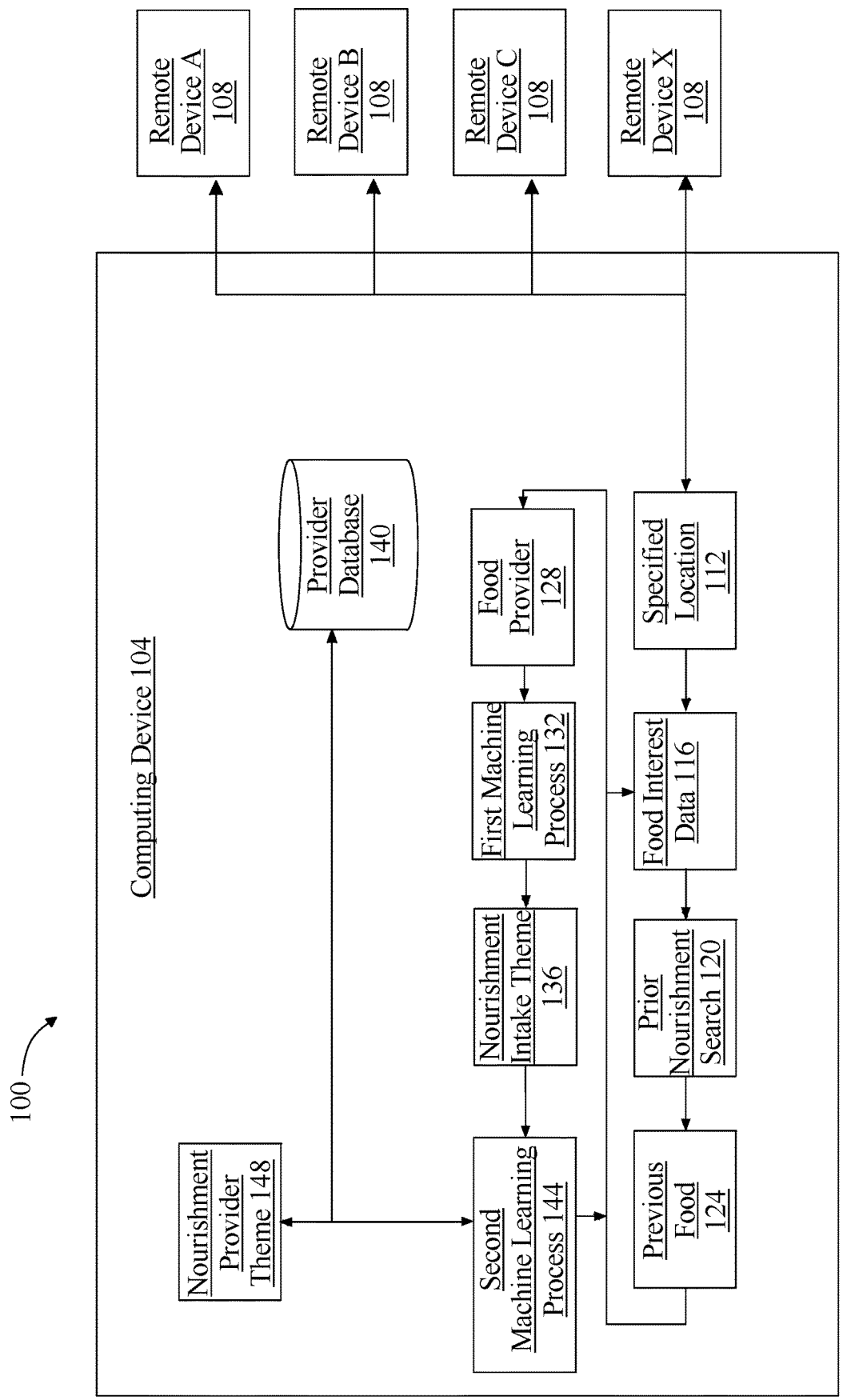
FIG. 1 is a block diagram illustrating an exemplary embodiment of a system for connecting food interests with food providers.

Referring now to FIG. 1, an exemplary embodiment of a system 100 for connecting food interests with food provider is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or connect with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or connect with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be transmitted to and/or from a computer and/or a computing device 104. Computing device 104 may include but is not limited to, for example, a computing device 104 or cluster of computing devices 104 in a first position and a second computing device 104 or cluster of computing devices 104 in a second position. Computing device 104 may include one or more computing devices 104 dedicated to data storage, security, dispersal of traffic for load balancing, and the like. Computing device 104 may distribute one or more computing tasks as described below across a plurality of computing devices 104 of computing device 104, which may operate in parallel, in series, redundantly, or in any other manner used for dispersal of tasks or memory between computing devices 104. Computing device 104 may be implemented using a "shared nothing" architecture in which data is cached at the operative, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive, from a first remote device of a plurality of remote devices located in a specified location, an input including food interest data. A "remote device," as used in this disclosure, is any additional computing device, such as a mobile device, laptop, desktop, computer, and the like. A "specified location," as used in this disclosure, is a particular geographical place and/or position. A specified location 112 may be based on a global positioning system (GPS) of a user and/or a remote device 108 operated by the user. A specified location 112 may include the latitude and/or longitude of a position where a user and/or a remote device 108 operated by the user is currently location, and/or a position where the user and/or the remote device 108 operated by the user may be located in the future. Computing device 104 is configured to receive information from each of a plurality of remote device 108 in a specified location 112 utilizing any network methodology as described herein. "Food interest data," as used in this disclosure, is a description of any eating habits and/or eating preferences that a user has. Eating habits may include any information pertaining to how many meals a user consumes each day, types of meals that a user consumes each day, amount of food consumed by a user at each meal, times of the day when a user eats meals each day, eating patterns, ingredient quality of meals, cooking habits of a user, food preparation habits of a user, fiscal limits and/or fiscal habits on meals, cuisine styles that a user prefers, and the like. Eating preferences may include any meals that a user likes or dislikes, any foods that a user likes or dislikes, any food allergies that a user has, any food intolerances that a user has, any foods that a user avoids, any diets and/or specialized way of eating that a user engages in, and the like. For instance and without limitation, food interest data 116 may include a description that a user follows a low-purine diet because of a previously diagnosed condition of gout, and as such the user avoids red meat, lamb, pork, organ meats, seafood, grain liquor, and high fructose corn syrup. In yet another non-limiting example, food interest data 116 may contain a description that a user follows a vegan diet and does not consume any animal ingredients because of ethical beliefs against consuming animals. In yet another non-limiting example, food interest data 116 may contain an indication that a user does not consume onions because the user does not like the taste of onions.

With continued reference to FIG. 1, food interest data 116 includes a prior nourishment search datum 120. A "prior nourishment search datum," as used in this disclosure, is data including any numerical, character, and/or symbolic data containing information describing a user's web browsing history. Web browsing history includes any web pages that a user has visited including any associated data containing page titles visited, time of visit, day of visit, and the like. For instance and without limitation, a prior nourishment search datum 120 may contain information pertaining to a user's search for "foods to eat with irritable bowel syndrome." In yet another non-limiting example, a prior nourishment search datum 120 may contain information describing a website that a user visited of a cafe where the user visited the menu page on the website for twenty minutes. In yet another non-limiting example, a prior nourishment search datum 120 may contain information describing a search a user performed looking for "Japanese establishments located within ten miles of my location." A prior nourishment search datum 120 may be shared with computing device 104 utilizing any network methodology as described herein.

With continued reference to FIG. 1, food interest data 116 includes a previous food provider acquisition 124. A "previous food provider acquisition," as used in this disclosure, is information describing any previous dining experiences a user had with a food provider 128. A "food provider," as used in this disclosure, is any provider of food and/or beverages intended for human consumption. A food provider 128 may include a café, a grocery store, a food hall, a food truck, a test kitchen, a meal-maker, a meal-delivery kit, a homemade meal prepared by a family member, friend, co-worker, acquaintance, and the like. A food provider 128 may provide for sale and/or purchase any food and/or beverages. A food provider 128 may contain sit down dining options, take-out dining options, meal delivery, online ordering, and the like. A previous food provider acquisition 124 includes any previous dining experiences a user had with a food provider 128, such as any meals a user ordered from a food provider 128, the number of times that a user visited a food provider 128 and/or consumed meals from a food provider 128 over a certain time frame and the like. For instance and without limitation, a previous food provider acquisition 124 may describe that a user visited a Greek cafe for lunch six times in the past month. In yet another non-limiting example, a previous food provider acquisition 124 may contain a description of a meal that a user ordered at an establishment when dining out with friends.

With continued reference to FIG. 1, food interest data 116 includes a diagnosis. A "diagnosis" as used in this disclosure, is the identification of the nature of an illness or other problem by examination of various signs, and/or symptoms. A diagnosis may contain a user reported diagnosis provided by a professional. A "professional," as used in this disclosure, is any person licensed or certified to provide health care services to natural persons. A professional may include but is not limited to a physician, a dentist, a nurse, a chiropractor, an optometrist, a physical or occupational therapist, a social worker, a clinical dietician, a clinical psychologist, a licensed professional counselor, a licensed marriage and family therapist, a pharmacist, a speech therapist, and the like. For instance and without limitation, food interest data 116 may contain a diagnosis such as rheumatoid arthritis, that a user was diagnosed with five year previously. Food interest data 116 may contain a description of one or more dietary patterns and/or ways of eating that a user has adopted due to a diagnosis. For instance and without limitation, food interest data 116 may contain a description that a user has coronary artery disease, and as such, the user is following a vegan diet. In yet another non-limiting example, food interest data 116 may contain a description that a user was previously diagnosed with multiple sclerosis, and the user follows a ketogenic diet to help manage multiple sclerosis. A diagnosis may contain a self-diagnosis, which may include a diagnosis made by a user. For example, a self-diagnosis may include a user who may self-diagnose a food intolerance after following an elimination diet and noticing symptoms that include bloating, gas, and diarrhea after consuming tomatoes. In yet another non-limiting example, a self-diagnosis may include a minor condition that may not be serious and that may be easily treatable with over the counter medications, such as a condition as head lice, skin abrasions, menstrual cramps, headache, or the common cold.

With continued reference to FIG. 1, computing device 104 receives food interest data 116 utilizing a questionnaire. A "questionnaire," as used in this disclosure, is an instrument containing a series of questions and/or other prompts for information regarding a user's eating habits. A questionnaire may contain a series of one or more open ended questions that may allow a user to type or write in an answer to a prompt for information. For example, a questionnaire may ask how many times a user ate out at an eatery in the past thirty days, what eateries the user ate out at, and what the user ordered at the eateries that the user ate out at. A questionnaire may contain a series of questions and/or prompts for information that may contain multiple answers that a user can choose to select such as to circle all foods that a user consumes on a daily basis, or to select one or more foods and/or beverages that a user does not like and doesn't consume frequently. A questionnaire may contain a series of photographs of various foods and/or meals and ask a user to selection photographs of foods and/or meals that a user enjoys eating, and to selection photographs of foods and/or meals that a user does not enjoy eating.

With continued reference to FIG. 1, computing device 104 is configured to generate as a function of a first machine-learning process 132, a nourishment intake theme for the first remote device, wherein the first machine-learning process 132 utilizes food interest data as an input, and outputs the nourishment intake theme. A "machine-learning process," as used in this disclosure, is a process that automatedly uses a body of data known as "training data" and/or a "training set" to generate an algorithm that will be performed by computing device 104 and/or a module to produce outputs given data provided as inputs; this is in contrast to a non-machine learning software program where the commands to be executed are determined in advance by a user and written in a programming language. "Training data," as used in this disclosure, is a set of examples that contain pairs of an input and a corresponding output, which are used to model relationships between two or more categories of data elements. Training data may be formatted to include labels, for instance by associating data elements with one or more descriptors corresponding to categories of data elements. Training data may not contain labels, where training data may not be formatted to include labels. A machine-learning process may include calculating one or more machine-learning algorithms and/or producing one or more machine-learning models. A machine-learning process may include a supervised machine-learning process that applies learned associations from the past to new data using labeled training data to predict future events. A supervised machine-learning process produces an inferred function to make predictions about output values. A supervised machine-learning process may include for example, active learning, classification, regression, and/or similarity learning. A machine-learning process may include an unsupervised machine-learning process where training data utilized to train the unsupervised machine-learning process may not be classified or labeled. An unsupervised machine-learning process may infer a function to describe a hidden structure from unlabeled data. An unsupervised machine-learning process may include for example, clustering, anomaly detection, neural networks, latent variable models, and the like. A machine-learning process may include a semi-supervised machine-learning process that may utilize a combination of both labeled and unlabeled training data. A semi-supervised machine-learning process may include generative models, low density separation, graph-based methods, heuristic approaches, and the like. A "nourishment intake theme," as used in this disclosure, is the identification of foods and/or beverages that a user habitually eats. A nourishment intake theme 136 may identify a particular diet that a user follows, such as a user who follows a gluten free diet, or a user who follows a dietary approach to stop hypertension (DASH) diet. A nourishment intake theme 136 may identify any foods and/or beverages that a user is not allowed to consume, such as a user with diabetes who is not allowed to consume any high fructose corn syrup. A nourishment intake theme 136 may identify recommended serving sizes of foods and/or nutrients that a user should consume, such as a user with pre-diabetes who is recommended to consume no more than 50 grams of carbohydrates each day. A nourishment intake theme 136 may identify one or more nutrients and/or minerals that a user may require, such as a user with hypothyroidism who may require additional iodine.

With continued reference to FIG. 1, computing device 104 generates a first machine-learning process 132 that utilizes food interest data 116 as an input, and outputs a nourishment intake theme 136 for each of a plurality of remote device 108. Computing device 104 trains a first machine-learning process 132 utilizing training data, including any of the training data as described herein. Training data may be obtained from previous iterations of generating a first machine-learning process 132, user inputs and/or questionnaire responses, expert inputs, and the like. Computing device 104 generates a first machine-learning process 132 utilizing a clustering algorithm. A "clustering algorithm," as used in this disclosure, is a machine-learning process that groups a set of objects that are more similar to each other to produce a cluster, than to those in other groups or clusters. A clustering algorithm may include generating one or more clustering models that may include but are not limited to connectivity models such as hierarchical clustering that builds models based on distance connectivity, centroid models such as k-means clustering that represent each cluster by a single mean vector, distribution models that contain clusters modeled using statistical distributions such as multivariate normal distributions, density models such as density based spatial clustering (DBSC) and ordering points to identify the clustering structure (OPTICS) which generate clusters as connected dense regions in data space, sub-space models such as biclustering where clusters are modeled with both cluster members and relevant attributes, group models, graph based models, signed graph models, neural models, and the like. A clustering algorithm generates a set of clusters, that contain all objects in a data set. A clustering algorithm may specify the relationship of clusters to each other. A clustering algorithm may generate hard clusters, where each object belongs to a cluster or not. A clustering algorithm may generate soft clusters, where each object belongs to each cluster to a certain degree. A clustering algorithm may include a strict partitioning cluster, where each object belongs to exactly one cluster. A clustering algorithm may include a strict partitioning cluster with outliers, where objects may not belong to any cluster, and may be considered an outlier. A clustering algorithm may include overlapping clustering, where objects may belong to more than one cluster. A clustering algorithm may include hierarchical clustering, where objects that belong to a child cluster also belong to a parent cluster. A clustering algorithm may include subspace clustering, where clusters do not overlap.

With continued reference to FIG. 1, computing device 104 is configured to detect a plurality of food provider 128 located within a specified location 112, wherein each of the plurality of food providers provides a nourishment provision. A food provider 128 includes any of the food provider 128 as described above in more detail. A food provider 128 may include for example, an eatery such as a Thai eatery located within a specified location 112. A food provider 128 may include a meal maker such as a home cook that prepares and sells meals to users within a specified location 112. A food provider 128 may be located within a specified location 112, when the food provider 128 is physically located within a specified location 112 and/or when a food provider 128 delivers and/or provides service within a specified location 112. Computing device 104 detects a plurality of food provider 128 by locating food provider 128 within a certain longitude and latitude distance of a specified location 112. Computing device 104 contains a provider database 140 that contains information pertaining to food provider 128 and the location of food provider 128 and areas that they service. Provider database 140 may be implemented, without limitation, as a relational database, a key-value retrieval datastore such as a NOSQL database, or any other format or structure for use as a datastore that a person skilled in the art would recognize as suitable upon review of the entirety of this disclosure. Such information may be updated utilizing any network methodology as described herein. For instance and without limitation, provider database 140 may contain an entry containing a description of a juice bar that has a physical location in Vero Beach, Fla., and which delivers to locations that include Fort Pierce, Port Saint Lucie, Stuart Sebastian, and Cocoa Beach. Computing device 104 detects a plurality of food provider 128 such as by generating a query to locate food provider 128 listed within provider database 140, to identify those who are located within and/or provide service to a specified location 112. A "query," as used in this disclosure, is any information utilized to detect a food provider 128. A query may be generated utilizing information about a specified location 112. For instance and without limitation, computing device 104 may generate a query to detect a food provider 128 located within the greater Miami area, when a specified location 112 identifies the East Coast of Florida. In yet another non-limiting example, computing device 104 may generate a query to detect a food provider 128 located in Anchorage, Ak. when a specified location 112 identifies southern Alaska. Food provider 128 stored within provider database 140 may be organized by locations in which they are located and/or serve.

With continued reference to FIG. 1, computing device 104 detects a plurality of food provider 128 using nourishment provisions available at food provider 128. A "nourishment provision," as used in this disclosure, is any food items available for purchase and/or sale offered by a food provider 128. A nourishment provision, may include a menu item, such as a list of meals and/or beverages available to purchase from a nourishment provision. For example, a menu items may contain meal options available for breakfast, lunch, dinner, and/or snacks, such as breakfast menu items that contains choices including a Mediterranean omelet, a berry smoothie, gluten free pancakes, a vegan yogurt parfait, and steel-cut gluten free oatmeal. A nourishment provision may include a list of one or more meal items available for purchase only at certain times of the day and/or only on specified days such as various special meals that may be available when certain foods are in season and/or available in various locations. For instance and without limitation, a nourishment provision may include a dinner entrée that contains King Salmon may only be available at a nourishment location from mid-May to early June, when King Salmon is in season. Computing device 104 locates a plurality of food provider 128 by evaluating nourishment provisions available by food provider 128. For instance and without limitation, a nourishment intake theme 136 that labels a user as following a vegetarian nourishment intake theme 136 may be utilized to eliminate nourishment provisions that contain seafood and/or meat. In yet another non-limiting example, a nourishment intake theme 136 label that specifies a user as following a Mediterranean style of eating may be utilized to locate nourishment provisions that contain Mediterranean foods including vegetables, fruits, whole grains, fish, nuts, seeds, and olive oil. Computing device 104 detects food provider 128 by searching food provider 128 contained within provider database 140. For instance and without limitation, computing device 104 generates a query to first locate food provider 128 located throughout the state of Rhode Island, and to detect those food providers 128 located throughout Rhode Island that provide nourishment provisions that contain dairy free nourishment provisions. Computing device 104 detects a plurality of food provider 128 by examining previous food provider acquisition 124, to identify previous food provider 128 a user interacted with and/or acquired meals from.

With continued reference to FIG. 1, computing device 104 generates as a function of a second machine-learning process 148, a nourishment provider theme 144 for each of a plurality of food provider 128 located within a specified location 112. A "nourishment provider theme," as used in this disclosure, is a label identifying cuisines and/or diets that a food provider 128 can create nourishment provisions for. A nourishment provider theme 144 may identify a certain cuisine that nourishment provisions offered by a food provider 128 fall into, such as Japanese, American comfort food, Korean cuisine, Mexican cuisine, and the like. In yet another non-limiting example, a nourishment provider theme 144 may identify one or more nourishment intake theme 136 that a food provider 128 can prepare meals for, such as by modifying and/or substituting currently available nourishment provisions. For instance and without limitation, a Japanese eatery that offers nourishment provisions that contain sushi rolls made with rice, may be able to modify the nourishment provisions to provide grain free sushi rolls made with cauliflower rice instead of traditional rice. In yet another non-limiting example, a seafood eatery that offers entrees that contain freshly caught seafood may be able to modify the nourishment provisions to offer vegetarian and/or vegan entrees that do not contain any freshly caught seafood. Information pertaining to the availability of ingredients to be substituted and/or nourishment provisions to be modified to comply with particular nourishment intake theme 136 may be stored within provider database 140.

With continued reference to FIG. 1, a second machine-learning process 148 includes any machine-learning process suitable for use as a first machine-learning process 132 as described above in more detail in reference to FIG. 1. A second machine-learning process 148 utilizes a nourishment provision as an input, and outputs a nourishment provider theme 144. Second machine-learning process 148 is calculated utilizing a classification algorithm. A "classification algorithm," as used in this disclosure, is a machine-learning model that sorts inputs into categories or bins of data. A classification algorithm may include linear classifiers such as Fisher's linear discriminant, logistic regression, Naïve Bayes classifier, perceptron, support vector machine, quadratic classifier, kernel estimation, k-nearest neighbor, boosting, random forest decision tree, neural network, and/or learning vector quantization. A classification algorithm is trained by computing device 104 utilizing any training data as described herein. Training data is obtained from previous iterations of calculating classification algorithm, expert inputs, user inputs and the like. Classification algorithm utilizes a nourishment provision as an input and outputs a nourishment provider theme 144.

With continued reference to FIG. 1, computing device 104 is configured to compare a remote device 108 having a nourishment intake theme 136 with a nourishment intake theme 136. Comparing includes determining if a nourishment provider theme 128 meets dietary recommendations contained within a nourishment intake theme 136. For instance and without limitation, a food provider 128 that offers ketogenic entrees may compare a nourishment intake theme 136 containing a ketogenic diet. In yet another non-limiting example, a food provider 128 that offers paleo entrees may compare a nourishment intake theme 136 including paleo nourishment themes, low-carbohydrate nourishment intake theme 136, grain free nourishment intake theme 136, and dairy free nourishment intake theme 136. Connecting includes identifying a food provider 128 that offers nourishment provisions that compare a nourishment intake theme 136 related to a remote device 108 with a remote device 108. Comparing includes identifying a food provider 128 that offers nourishment provisions that fit one or more nourishment intake theme 136. Comparing may include generating a list of food provider 128 that compare to one or more remote device 108. For instance and without limitation, computing device 104 may identify a food provider 128 that contains a nourishment provider theme 144 of gluten free meals that compares nourishment intake theme 136 that include gluten free, wheat free, standard American diet, rye free, vegetarian, pescatarian, and the like.

With continued reference to FIG. 1, computing device 104 supports transmission of a nourishment provision as a function of comparing a first nourishment intake theme to a nourishment provider theme. Supporting transmission includes using any network methodology as described herein to share with a remote device 108 information that identifies a food provider 128 that compares a nourishment intake theme 136 identified for the remote device 108. Supporting transmission includes sharing advertising material with a remote device 108 utilizing any network methodology as described herein. Advertising material includes any data transmitted identifying a food provider 128. For instance and without limitation, computing device 104 supports transmission of data to a remote device 108, identifying three food provider 128 that compares a nourishment identified for the remote device 108. Computing device 104 supports transmission of data to a remote device 108 utilizing any network methodology as described herein. Computing device 104 is configured to support transmission of default food provider located within a specified location 112. A "default food provider," as used in this disclosure, is any food provider 128 that is located within a specified location 112, but that does not contain a nourishment provision that compares a nourishment intake theme 136 identified for a remote device 108. For instance and without limitation, a remote device 108 that contains a nourishment intake theme 136 such as a vegetarian theme may receive default food provider located within a specified location 112 of the remote device 108, but the food provider 128 may not necessarily offer nourishment provisions that comply with the vegetarian theme. Computing device 104 is configured to block transmission of nourishment provisions that fall outside a nourishment intake theme 136. Nourishment provisions fall outside a nourishment intake theme 136 when the nourishment provisions do not compare the nourishment intake theme 136. For instance and without limitation, a food provider 128 may offer five dinner entrees, of which three entrees compare with a nourishment intake theme 136 and two entrees do not compare with the nourishment intake theme 136. In such an instance, computing device 104 supports transmission of the three entrees that compare the nourishment intake theme 136, and computing device 104 blocks transmission of the two entrees that do not compare the nourishment intake theme 136.

Figure 2:
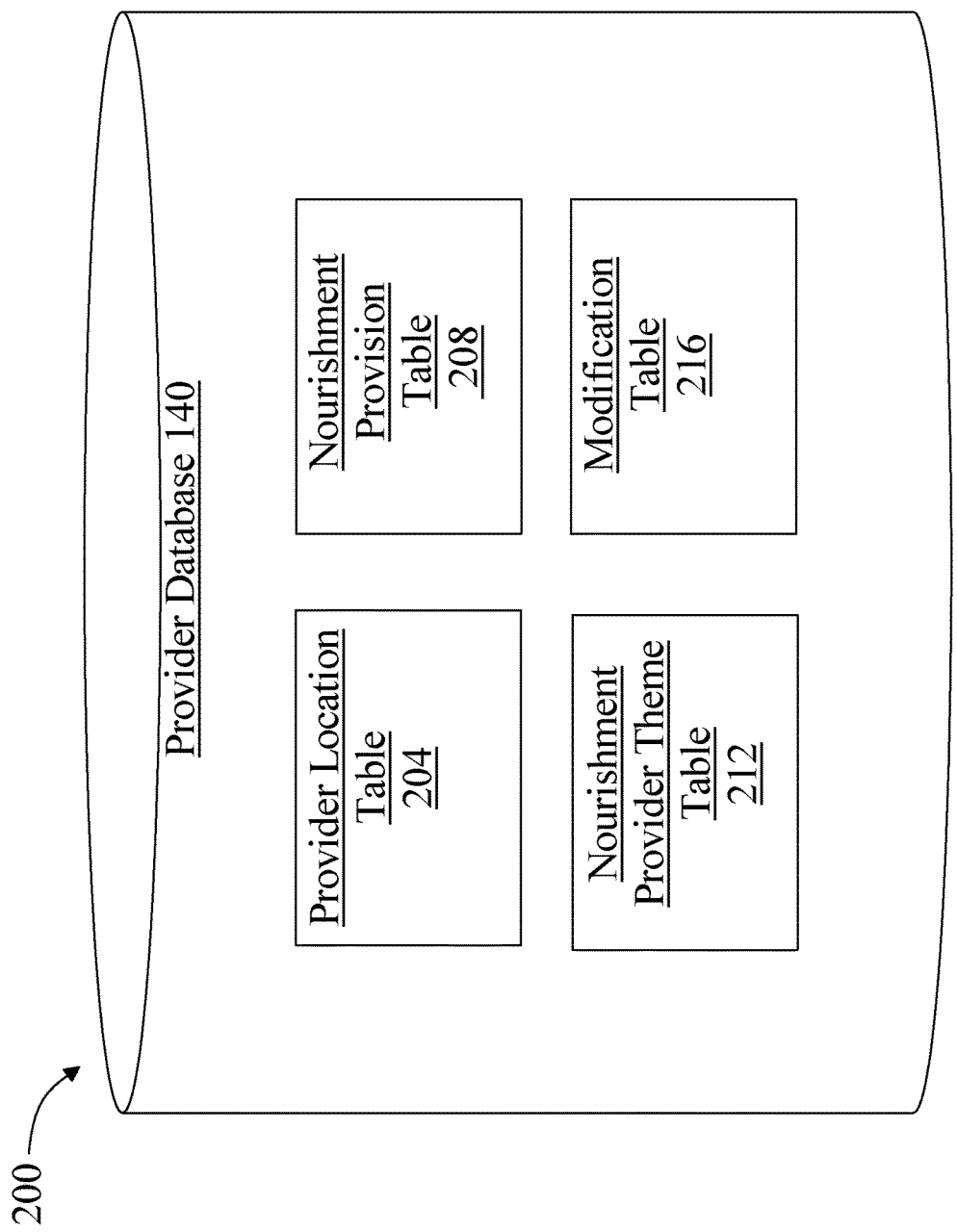
FIG. 2 is a block diagram illustrating an exemplary embodiment of a provider database.

Referring now to FIG. 2, an exemplary embodiment 200 of provider database 140 is illustrated. Provider database 140 may be implemented as any data structure suitable for use as described above in more detail in reference to FIG. 1. One or more tables contained within provider database 140 may include provider location table 204; provider location table may contain information describing a specified location 112, containing information detailing where a food provider 128 is located and/or areas where a food provider 128 delivers to and/or provides services to. For instance and without limitation, provider location table 204 may contain information detailing that a food provider 128 is located in Oklahoma City, and provides service and/or delivery to surrounding towns that include Bethany, Yukon, Moore, McLoud, and Edmond. One or more tables contained within provider database 140 may include nourishment provision table 208; nourishment provision table 208 may contain information pertaining to nourishment provisions available at a food provider 128, including for example, one or more menu items. For instance and without limitation, nourishment provision table 208 may contain a list of nourishment provisions available at food provider 128 for lunch, which include a cobb salad, a Caesar salad, a turkey club sandwich, a California chicken sandwich, and a taco salad. One or more tables contained within provider database 140 may include nourishment provider theme table 212; nourishment provider theme table 212 may contain information describing a nourishment provider theme 144 of one or more food provider 128. For instance and without limitation, nourishment provider theme 144 table 212 may contain an entry describing a food provider 128 as having a nourishment provider theme 144 of gluten free and vegan Mediterranean style nourishment provisions. One or more tables contained within provider database 140 may include modification table 216; modification table 216 may contain information describing one or more modifications a food provider 128 can make regarding nourishment provisions and/or creating nourishment provisions that fit one or more nourishment provider theme 144. For instance and without limitation, modification table 216 may contain an entry describing a food provider 128 that has a nourishment provision that contains cod with risotto and vegetables that can be modified to create both a vegetarian and/or a vegan nourishment provision.

Figure 3:
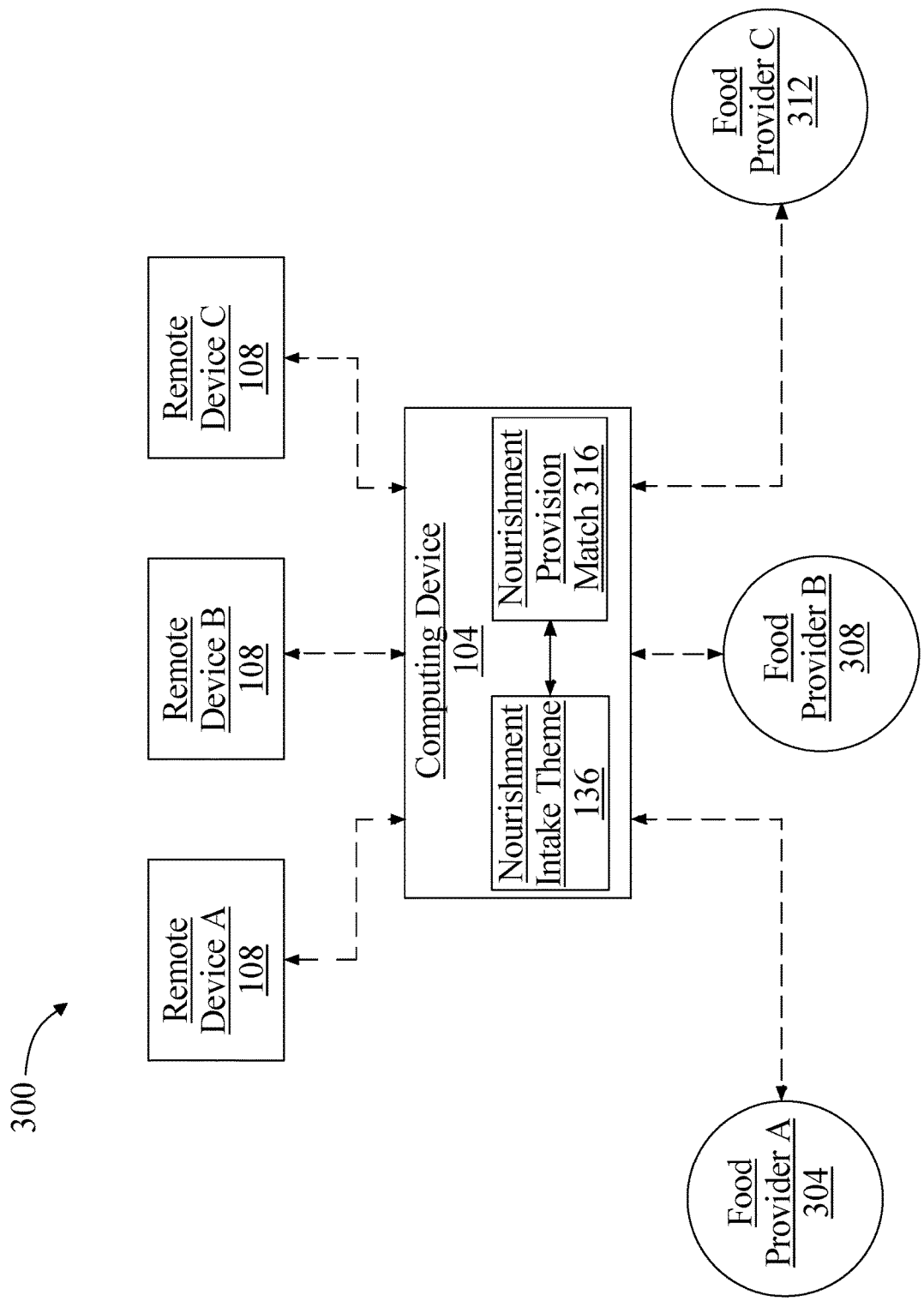
FIG. 3 is a diagrammatic representation of comparing a remote device with a food provider.

Referring now to FIG. 3, an exemplary embodiment of comparing nourishment intake theme 136 with food provider 128 is illustrated. Computing device 104 receives from each of a plurality of remote device 108 located in a specified location 112, a plurality of inputs containing food interest data 116, as described above in more detail in reference to FIG. 1. In an embodiment, a plurality of remote device 108, such as remote device 108 A, remote device 108 B, and remote device 108 C may be in communication with computing device 104. Computing device 104 generates as a function of a first machine-learning process 132, a nourishment intake theme 136 for each of a plurality of remote device 108. A first machine-learning process 132 includes any of the machine-learning processes as described above in more detail in reference to FIG. 1. Computing device 104 detects a plurality of food provider 128 located within a specified location 112 providing a nourishment provision. A nourishment provision includes any of the nourishment provisions as described above in more detail in reference to FIG. 1. For instance and without limitation, computing device 104 detects food provider 128 A 304, food provider 128 B 308, and food provider 128 C, 312, contained within a specified location 112. A specified location 112 includes any of the specified location 112 as described above in more detail in reference to FIG. 1, including a particular geographical region or location. Computing device 104 generates as a function of a second machine-learning process 148, a nourishment provider theme 144 148 for each of a plurality of food provider 128 located within a specified location 112. For instance and without limitation, computing device 104 identifies a first nourishment provider theme 144 for food provider A 128, a second nourishment provider theme 144 for food provider B 128, and a third nourishment provider theme 144 for food provider C 128. Second machine-learning process 148 includes any of the second machine-learning process 148 as described above in more detail in reference to FIG. 1. Second machine-learning process 148 utilizes a nourishment provision as an input, and outputs a nourishment provider theme 144. Computing device 104 compares a remote device 108 having a nourishment intake theme 136 with a food provider that offers a nourishment provision 316 that compares a nourishment intake theme 136. For instance and without limitation, computing device 104 may compare a nourishment provision 316 offered by food provider A 304 to a nourishment intake theme 136 of remote device 108 B. In such an instance, computing device 104 supports transmission of the nourishment provision compare 316 offered by food provider A 304 to remote device 108 B, utilizing any network methodology as described herein.

Figure 4:
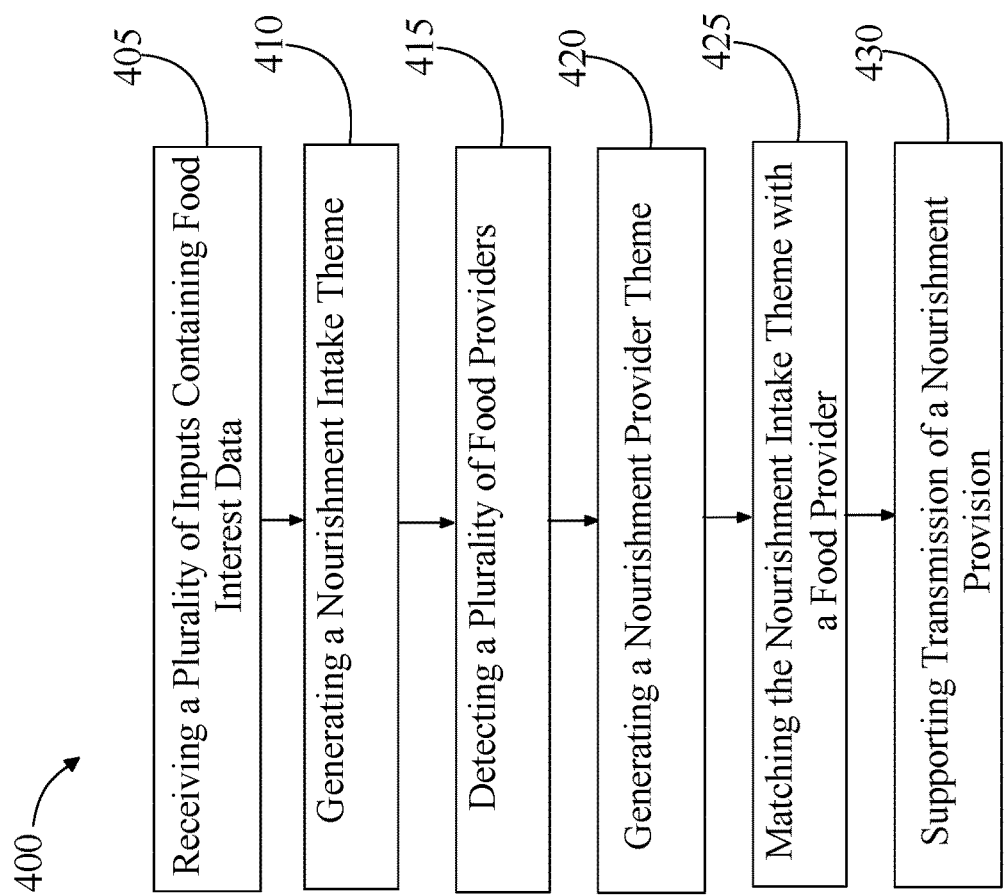
FIG. 4 is a process flow diagram illustrating an exemplary embodiment of a method of connecting food interests with food providers.

Referring now to FIG. 4, an exemplary embodiment of a method 400 for connecting food interests with food provider 128 is illustrated. At step 405, computing device 104 receives from a first remote device of a plurality of remote device 108 located in a specified location 112, a plurality of inputs containing food interest data 116. A remote device 108 includes any of the remote device 108 as described above in more detail in reference to FIG. 1. For instance and without limitation, a remote device 108 may include a mobile computing device. In yet another non-limiting example, a remote device 108 may include an additional computing device, including any device suitable for use as computing device 104 as described above in more detail in reference to FIG. 1. A specified location 112 includes any of the specified location 112 as described above in more detail in reference to FIG. 1. A specified location 112 includes a particular geographical place and/or position. For instance and without limitation, a specified location 112 may include a geographical place such as Boston, Mass. In yet another non-limiting example, a specified location 112 may include a GPS location, such as Coral Way Village, located in Westchester, Fla. Computing device 104 receives from each of a plurality of remote device 108, utilizing any network methodology as described herein, a plurality of inputs containing food interest data 116. Food interest data 116 includes any of the food interest data 116 as described above in more detail in reference to FIG. 1. Food interest data 116 contains a description of any eating habits and/or eating preferences that a user has. For instance and without limitation, food interest data 116 may contain an input specifying that a user consumes a raw foods diet, and consumes foods such as fresh fruits, raw vegetables, sprouted grains, nut and seed butter, and cold pressed coconut oil. In yet another non-limiting example, food interest data 116 may contain an input specifying that a user only eats meals between the hours of 11:00 am and 4:00 pm every day, the other hours of the day the user engages in intermittent fasting.

With continued reference to FIG. 4, food interest data 116 includes a prior nourishment search datum 120. A prior nourishment search datum 120 includes any of the prior nourishment search datum 120 as described above in more detail in reference to FIG. 1. A prior nourishment search datum 120 may include a user's web browsing history, including for example any food provider 128 that a user may have search for, or any questions relating to food provider 128 that a user researched. For instance and without limitation, a prior nourishment search datum 120 may contain a web browsing search that a user entered looking for "recommended barbeque eateries located in Dallas, Tex." In yet another non-limiting example, a prior nourishment search datum 120 may contain a web browsing history that contains an input describing that a user visited a website for a vegetarian eatery and browed through the online menu for twenty seven minutes. Food interest data 116 contains a previous food provider acquisition 124. A previous food provider acquisition 124 includes any of the previous food provider acquisition 124 as described above in more detail in reference to FIG. 1. A previous food provider acquisition 124 may contain a list of all meals that a user consumed over the course of the previous two weeks. In yet another non-limiting example, a previous food provider acquisition 124 may contain a description of a meal that a user consumed from a food provider 128 during the previous week. Food interest data 116 includes a diagnosis. A diagnosis includes any of the diagnoses as described above in more detail in reference to FIG. 1. A diagnosis may include a description of a medical condition that a user was diagnosed with by a medical professional. For instance and without limitation, a diagnosis may contain a description of a medical condition such as ulcerative colitis that a user was diagnosed with three years prior, by a medical professional such as a gastroenterologist. A diagnosis may include information pertaining to a self-diagnosis made by a user, such as when a user may self-diagnose a self-limiting condition that resolves on its own without treatment or can be treated with one or more over the counter treatment options. For instance and without limitation, a diagnosis may include a self-limiting condition such as a migraine headache, that a user treated with a caffeine pill.

With continued reference to FIG. 4, computing device 104 receives information pertaining to food interest data 116 utilizing a questionnaire. A questionnaire includes any of the questionnaires as described above in more detail in reference to FIG. 1. For instance and without limitation, computing device 104 may transmit to a remote device 108 a questionnaire that includes a list of hundreds of the most commonly diagnosed medical conditions and ask a user to select any of the diagnosed medical conditions that the user has previously and/or is currently diagnosed with. In yet another non-limiting example, a questionnaire may include a prompt for information from a user, whereby a questionnaire may display photographs of individual foods and/or meals, and ask a user to select any foods and/or meals that a user likes to consume, and to select any foods and/or meals that a user dislikes to consume.

With continued reference to FIG. 4, at step 410, computing device 104 generates as a function of a first machine-learning process 132, a nourishment intake theme 136 for each of the plurality of remote device 108. A nourishment intake theme 136 identifies foods and/or beverages that a user habitually eats, as described above in more detail in reference to FIG. 1. For instance and without limitation, a nourishment intake theme 136 may identify a particular eating pattern that a user follows based on foods and/or beverages that a user habitually consumes. For example, a user who consumes foods that include meats, vegetables, fruits, and dairy free milk may be identified as having a nourishment intake theme 136 of paleo. In yet another non-limiting example, a user who consumes high-fats, moderate proteins and very low carbohydrates may be identified as having a nourishment intake theme 136 of ketogenic. A nourishment intake theme 136 is identified by calculating a first machine-learning process 132. A first machine-learning process 132 includes any of the machine-learning processes as described above in more detail in reference to FIG. 1. A first machine-learning process 132 includes calculating a clustering algorithm. A clustering algorithm may be implemented as any of the clustering algorithms as described above in more detail in reference to FIG. 1.

With continued reference to FIG. 4, at step 415, computing device 104 detects a plurality of food provider 128 located within a specified location 112 providing a nourishment provision. Computing device 104 detects a plurality of food provider 128, by finding food provider 128 that are located within and/or provide service within a specified location 112. Computing device 104 generates a query to locate food provider 128 contained within provider database 140 that offer nourishment provisions within a specified location 112. For instance and without limitation, a specified location 112 may specify San Diego, Calif. In such an instance, computing device 104 generates a query to detect food provider 128 that are located within San Diego, and/or that deliver and/or provide service to users located within San Diego. Food provider 128 may be listed and contained within provider database 140 based on specified location 112 information as described above in more detail in reference to FIG. 1. Computing device 104 detects a plurality of food provider 128 located within a specified location 112 by locating nourishment provisions available at food provider 128. Information pertaining to nourishment provisions available at food provider 128 may be stored within provider database 140 and may be updated utilizing any network methodology as described herein. Computing device 104 may examine nourishment provisions to examine if any of the nourishment provisions comply with a nourishment provider theme 144, and/or can be modified to comply with the nourishment provider theme 144. For instance and without limitation, a food provider 128 that offers nourishment provisions that are all cooked in peanut oil may be unable to modify a nourishment provision that is not cooked in peanut oil and/or that is not cross-contaminated with peanut oil. In such an instance, computing device 104 may eliminate such a food provider 128. In yet another non-limiting example, a food provider 128 that offers nourishment provisions that include grain free sushi rolls may be detected as providing a nourishment provision that complies with a low-carbohydrate nourishment intake theme 136 for a user with pre-diabetes who is significantly limiting intake of carbohydrates.

With continued reference to FIG. 4, at step 420, computing device 104 generates as a function of a second machine-learning process 148 a nourishment provider theme 144 for each of a plurality of food provider 128 located within a specified location 112. A nourishment provider theme 144 includes any of the nourishment provider theme 144s as described above in more detail in reference to FIG. 1. A nourishment provider theme 144 identifies cuisines and/or diets that a food provider 128 can create nourishment provisions for. For instance and without limitation, a nourishment provider theme 144 may identify a food provider 128 that offers nourishment provisions that are grain free, vegan, dairy free, gluten free, and vegetarian. In yet another non-limiting example, a nourishment provider theme 144 may identify a food provider 128 that offers Mexican nourishment provisions that can be modified to be dairy free. Information pertaining to modifications of nourishment provider theme 144s may be stored within provider database 140 as described above in more detail in reference to FIG. 2. A food provider 128 may contain a nourishment provider theme 144 that identifies more than one cuisine, diets, and/or eating patterns that nourishment provisions may be modified for and/or apply to. For instance and without limitation, a food provider may prepare that are gluten free, nut free, soy free, vegetarian, and onion free. Second machine-learning process 148 includes any of the machine-learning processes as described above in more detail in reference to FIG. 1. Second machine-learning process 148 may include generating a classification algorithm, including any of the classification algorithms as described above in more detail in reference to FIG. 1. Second machine-learning process 148 utilizes a nourishment provision as an input, and outputs a nourishment provider theme 144.

With continued reference to FIG. 4, at step 425, computing device 104 compares a first remote device 108 having a first nourishment intake theme 136 with a nourishment provider theme 128. Comparing includes identifying food provider 128 located within a specified location 112 that offer nourishment provisions that meet and/or exceed a nourishment intake theme 136. Comparing includes examining a nourishment provider theme 144 to determine if a nourishment provider theme 144 can be adjusted to accommodate a nourishment intake theme 136. For instance and without limitation, computing device 104 identifies a food provider 128 with a nourishment theme such as Italian American and comparing includes determining if one or more nourishment provisions can be modified to be made gluten free to compare a nourishment intake theme 136 of gluten free. In yet another non-limiting example, comparing includes finding food provider 128 that offer nourishment provisions that are low in fermentable oligosaccharides, disaccharides, monosaccharides, and polyols (FODMAPS) to meet the needs of a nourishment intake theme 136 of low-FODMAP.

With continued reference to FIG. 4, at step 430, computing device 104 supports transmission of a nourishment provision as a function of comparing a first nourishment intake theme to a nourishment provider theme. Supporting transmission includes transmission to a remote device 108 information identifying a food provider 128 that contains a nourishment provision that compares a nourishment intake theme 136. Computing device 104 transmits information identifying a food provider 128 utilizing any network methodology as described herein. Computing device 104 may transmit information such as advertising materials that may promote and/or display one or more food provider 128 that contain nourishment provisions that compare a nourishment intake theme 136. Advertising materials include any marketing communications that may contain sponsored messages to promote a food provider 128 and/or to sell nourishment provisions offered by a food provider 128. Computing device 104 supports transmission of default food provider located within a specified location 112. A default food provider includes any of the default food provider as described above in more detail in reference to FIG. 1. For example, a default food provider may include a food provider 128 that does not have any nourishment provisions that compare a nourishment intake theme 136. In yet another non-limiting example, a default food provider may include any food provider 128 located within a specified location 112, which may have not yet been analyzed to determine if the default food provider offers nourishment provisions that compare a nourishment intake theme 136. Computing device 104 is configured to block transmission of nourishment provisions outside a nourishment intake theme 136. Blocking transmission includes not transmitting to a remote device 108, information pertaining to nourishment provisions that do not compare a nourishment intake theme 136. For instance and without limitation, computing device 104 blocks transmission of nourishment provisions that contain dairy and that cannot be modified to remove and/or modify dairy for a dairy free nourishment intake theme 136. In such an instance, computing device 104 supports transmission of nourishment provisions that do not contain dairy offered by the same food provider 128.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
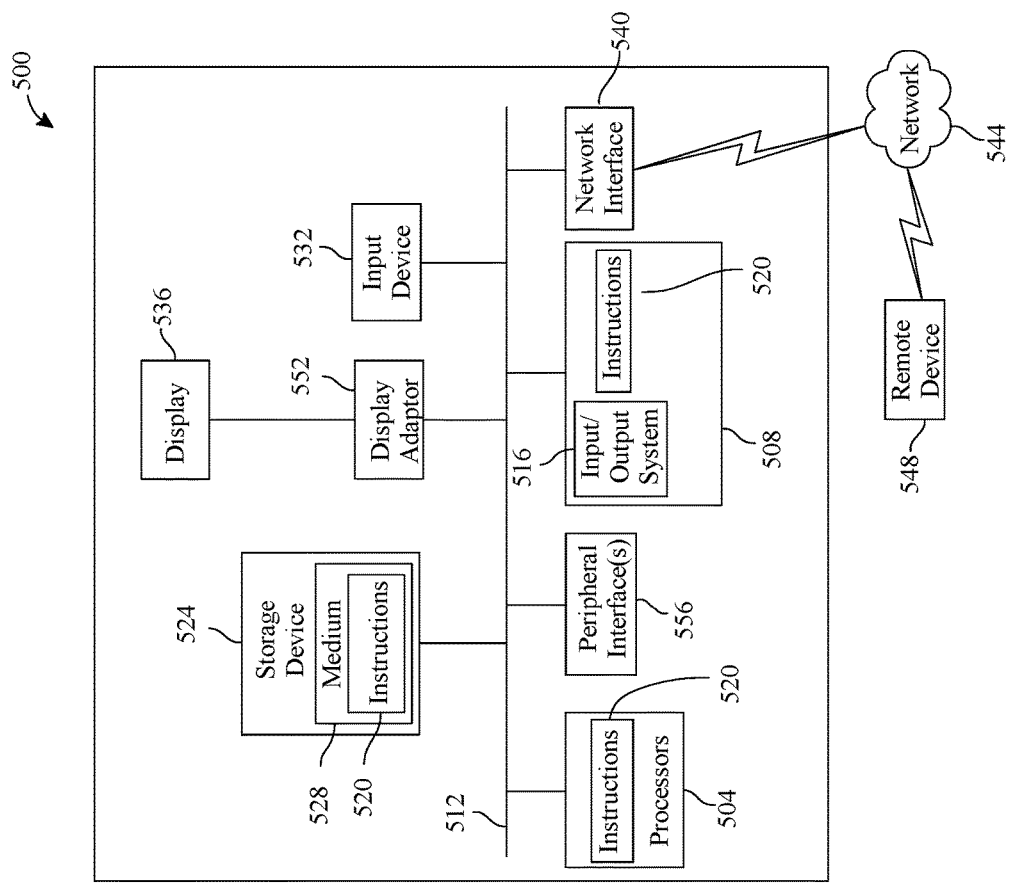
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for connecting food interests with food providers, the system comprising a computing device, the computing device designed and configured to:
   receive, from a first remote device of a plurality of remote devices located in a specified location, food interest data comprising:
      a user reported diagnosis, wherein the user reported diagnosis is diagnosed and provided by a medical professional, identifying a non-food related medical condition; and
      at least a prior nourishment search datum based on food interests linked to a non-food related medical condition;
   train a clustering machine-learning process with training data comprising:
      user inputs including user questionnaire responses, wherein the user questionnaire contains a series of photographs of various foods for user selection; and
      expert inputs;
   generate a clustering machine-learning model configured to:
      receive the food interest data as an input, and output a nourishment intake theme, as a function of the clustering machine-learning process, wherein the clustering machine learning model comprises a connectivity model including hierarchical clustering;
   detect a plurality of food providers located within the specified location by generating a query in a provider database, wherein each of the plurality of food providers provides a nourishment provision;
   generate a classification machine-learning model, as a function of a classification machine-learning process, configured to receive a nourishment provision for each food provider of the plurality of food providers located within the specified location; and wherein the classification machine-learning model utilizes a respective nourishment provision from each of the plurality of food providers located within the specified location as inputs and outputs a nourishment provider theme for each food provider of the plurality of food providers as a function of a comparison between each category in the plurality of categories and the received nourishment provisions;
   compare a first nourishment intake theme from a plurality of nourishment intake themes generated by the trained clustering machine-learning model with the nourishment provider theme generated by the trained classification machine-learning model; and
   transmit the nourishment provision to a first respective food provider from the plurality of detected food providers as a function of the comparison of the first nourishment intake theme to the nourishment provider theme;
   generate an advertisement material for a second respective food provider from the plurality of detected food providers as a function of the comparison of the first nourishment intake theme to the nourishment provider theme; and
   transmit the advertisement material to the first remote device.

2. The system of claim 1, wherein the food interest data further comprises a previous food provider acquisition.

3. The system of claim 1, wherein the computing device is further configured to detect the plurality of food providers as a function of nourishment provisions available at food providers.

4. The system of claim 1, wherein the computing device is further configured to support transmission of default food providers located within the specified location.

5. The system of claim 1, wherein the computing device is further configured to block transmission of nourishment provisions outside the nourishment intake theme.

6. A method of connecting food interests with food providers, the method comprising:
   receiving by a computing device, from a first remote device of a plurality of remote devices located in a specified location, food interest data comprising:
      a user reported diagnosis, wherein the user reported diagnosis is diagnosed and provided by a medical professional, identifying a non-food related medical condition; and
      a prior nourishment search datum based on food interests linked to a non-food related medical condition;
   training by the computing device, a clustering machine-learning process with training data comprising user inputs including user questionnaire responses, wherein the user questionnaire contains a series of photographs of various foods for user selection; and expert inputs;
   generating, by the computing device, a clustering machine-learning model configured to receive the food interest data as an input, and output a nourishment intake theme, as a function of the clustering machine-learning process, wherein the clustering machine learning model comprises a connectivity model including hierarchical clustering
   detecting by the computing device, a plurality of food providers located within the specified location by generating a query in a provider database, wherein each of the plurality of food providers provides a nourishment provision;
   generating by the computing device a classification machine-learning model, as a function of a classification machine-learning process, configured to receive a nourishment provision for each food provider of the plurality of food providers located within the specified location; and wherein the classification machine-learning model utilizes a respective nourishment provision from each of the plurality of food providers located within the specified location as inputs and outputs a nourishment provider theme for each food provider of the plurality of food providers as a function of a comparison between each category in the plurality of categories and the received nourishment provisions;
   comparing by the computing device, a first nourishment theme from a plurality of nourishment intake themes generated by the clustering trained machine-learning model with the nourishment provider theme generated by the classification trained machine-learning model; and transmitting by the computing device, the nourishment provision to a respective food provider as a function of the comparison of the first nourishment intake theme to the nourishment provider theme;
generating, by the computing device, an advertisement material for a second respective food provider from the plurality of detected food providers as a function of the comparison of the first nourishment intake theme to the nourishment provider theme; and
transmit, by the computing device, the advertisement material to the first remote device.

7. The method of claim 6, wherein the food interest data further comprises a previous food provider acquisition.

8. The method of claim 6, wherein detecting the plurality of food providers further comprises evaluating nourishment provisions available at food providers.

9. The method of claim 6 further comprising supporting transmission of default food providers located within the specified location.

10. The method of claim 6 further comprising blocking transmission of nourishment provisions outside the nourishment intake theme.

* * * * *